United States Patent
McNair

(10) Patent No.: US 10,653,368 B1
(45) Date of Patent: May 19, 2020

(54) DETERMINING WHEN TO EMIT AN ALARM

(71) Applicant: Cerner Innovation, Inc., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 768 days.

(21) Appl. No.: 14/481,436

(22) Filed: Sep. 9, 2014

Related U.S. Application Data

(60) Provisional application No. 61/875,344, filed on Sep. 9, 2013.

(51) Int. Cl.

| | |
|---|---|
| *G01N 33/48* | (2006.01) |
| *G01N 33/50* | (2006.01) |
| *A61B 5/00* | (2006.01) |
| *A61B 5/0205* | (2006.01) |
| *A61B 5/021* | (2006.01) |

(Continued)

(52) U.S. Cl.
CPC .............. *A61B 5/746* (2013.01); *A61B 5/01* (2013.01); *A61B 5/021* (2013.01); *A61B 5/02055* (2013.01); *A61B 5/031* (2013.01); *A61B 5/14542* (2013.01); *A61B 5/486* (2013.01); *A61B 5/4839* (2013.01); *A61B 5/4848* (2013.01); *A61B 5/726* (2013.01); *A61B 5/7264* (2013.01); *A61B 5/7282* (2013.01); *A61M 16/0051* (2013.01); *A61M 16/0057* (2013.01); *A61M 16/04* (2013.01); *A61B 5/024* (2013.01);

(Continued)

(58) Field of Classification Search
None
See application file for complete search history.

(56) References Cited

U.S. PATENT DOCUMENTS 3,863,625 A * 2/1975 Viglione ............ A61B 5/04014
600/545
5,319,355 A * 6/1994 Russek ................ A61B 5/0002
128/202.22

(Continued)

OTHER PUBLICATIONS

Qu et al. A seizure warning system for long-term epilepsy monitoring. Neurology, vol. 45, 1995, pp. 2250-2254.*

*Primary Examiner* — Russell S Negin
(74) *Attorney, Agent, or Firm* — Shook, Hardy & Bacon L.L.P.

(57) ABSTRACT

Systems and methods are provided for evaluating an alarm condition for a monitored patient in a population of one or more patients. One or more physiological parameters pertaining to the patient, or physiological variables, are used to form a time series describing the patient status. A dimension parameter such as a time series roughness statistic or a fractal dimension is used to estimate a dimension decision statistic over time. The dimension decision statistic is used as a measure of physiological condition. The dimension decision statistic may be compared to a threshold to determine a region of operation for the dimension of the physiological variable. The dimension decision statistic is used in an embodiment in combination with the underlying raw physiological variable value to reduce the rate of false alarms, to increase the frequency of missed detections, and to aid diagnostic decision making and to aid the formation of a crisis action plan.

20 Claims, 7 Drawing Sheets

(51) Int. Cl.
  *A61B 5/145* (2006.01)
  *A61B 5/03* (2006.01)
  *A61B 5/01* (2006.01)
  *A61M 16/04* (2006.01)
  *A61M 16/00* (2006.01)
  *A61B 5/08* (2006.01)
  *A61B 5/024* (2006.01)

(52) U.S. Cl.
  CPC ........ *A61B 5/0816* (2013.01); *A61M 2205/15* (2013.01); *A61M 2205/18* (2013.01)

(56) References Cited

U.S. PATENT DOCUMENTS

| | | | |
|---|---|---|---|
| 6,438,419 B1 * | 8/2002 | Callaway | A61N 1/3925 600/508 |
| 2002/0103512 A1 * | 8/2002 | Echauz | A61B 5/0482 607/9 |
| 2006/0132190 A1 * | 6/2006 | Driediger | G01R 23/005 327/47 |
| 2006/0135877 A1 * | 6/2006 | Giftakis | A61B 5/0402 600/513 |
| 2012/0050045 A1 * | 3/2012 | Hively | G06K 9/00536 340/573.1 |
| 2012/0095304 A1 * | 4/2012 | Biondi | G16H 50/20 600/301 |

\* cited by examiner

DETERMINING WHEN TO EMIT AN ALARM

CROSS-REFERENCE TO RELATED APPLICATIONS

This application claims the benefit of U.S. Provisional Application No. 61/875,344, titled "DIMENSION STATISTICS FOR DECISION PROCESSING," filed Sep. 9, 2013, which is hereby expressly incorporated by reference in its entirety.

INTRODUCTION

When a patient's clinical condition is deemed sufficiently abnormal, a number of devices or technologies are provided by medical staff to continuously monitor patient physiology. This allows bedside staff to check patient condition by observing physiological measures such as temperature, blood pressure, respiration rate, blood oxygen saturation, pulse rate, and other vital signs, or variables. A dangerously high or low value of a measure alerts staff to investigate causes, and potential interventions, to alleviate imminent ill-effects of an extreme physiological value.

Unfortunately, for a given patient, staff may not be at bedside observing the complete physiological picture when a physiological measure approaches a dangerous level. For this reason, a device or technology that measures a physiological level may use an alarm threshold so that if the physiological measure is above or below the alarm threshold, an alarm tone or other form of notification is emitted to draw attention to the level indicated by the device or technology, and perhaps also to summon staff to the bedside.

Multiple problems are created by poor physiological measures. Too often, alarms, which can include notifications, are presented to a clinician when a measurement is out of bounds relative to a threshold but the underlying physiological indicator for the monitored patient is not a concern for a well-informed clinician. For example, the physiological measure for a particular patient may be abnormal, but typical for this patient, and stable; the physiological measure is out of bounds because a procedure is being performed, or because a probe has lost its source of signal, or because a probe is experiencing an error condition unrelated to patient physiology, etc. Such errant alarms effectively "train" clinicians that most alarms are a nuisance i.e., a message that the device measuring a physiological parameter needs to be attended to, effectively distracting the clinician to focus on a device rather than on patient care. Often, as a result, alarms are disabled, thresholds are widened to lessen the frequency of alarms, and legitimate alarms are ignored. Clinicians become desensitized to alarms, safety is eroded, and adverse outcomes increase. There is a general continuing need for improving physiological signal processing in support of clinical observation and decision making, so that false alarms are reduced, sensitivity to adverse physiology is increased, appropriate responses are aided, and inappropriate requests are made less frequently.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The present invention is defined by the claims.

Systems, methods, and computer-readable media are provided for processing one or more physiological measurements or other physiological variables for clinical decision making. For example, an embodiment determines that an alarm condition or a maintenance condition is present for a given patient. One or more physiological variables such as blood oxygen saturation level, a respiration rate, an Electro-Encephalogram (EEG) signal, other vital signs, biomarker(s), or an optical image of the patient are monitored to form a time series of the one or more physiological variable values. A dimension parameter, such as a result that quantifies the roughness of the time series, or the fractal dimension of the time series, is estimated. A decision statistic based on the dimension parameter estimate is provided for interpretation and logical evaluation. An embodiment forms the decision statistic by calculating a trend statistic such as a moving sum over a moving window of dimension parameter estimates. The decision statistic is compared to a breakpoint threshold to determine if the current value exceeds the threshold. An indication of a decision region, such as a field indicating that an alarm condition is present, is stored if it is determined that the decision statistic has crossed a breakpoint threshold. An embodiment forms a physiological variable decision statistic, which reflects the current value of the physiological variable itself. In an embodiment, an alarm is indicated if both the physiological variable decision statistic has crossed an alarm threshold level and if the decision statistic has crossed the breakpoint threshold.

In one aspect, a computer performs a method to evaluate an alarm condition. In an embodiment, each patient in a population of one or more patients is monitored for a physiological variable level. An alarm, which may include any type of notification, is generated for a patient when a threshold-crossing value of a physiological variable is experienced, and a trend statistic based on a fractal dimension estimate exceeds a breakpoint-crossing value.

In another aspect, a physiological variable is used for clinical decision making. In an embodiment, a physiological variable of a patient is monitored, forming a series of physiological variable levels. A sequence of dimension parameter estimates are formed with a first estimate of the dimension parameter being formed for a first time interval, and a second estimate being formed for a second time interval. A decision statistic is formed based on the first and second estimate. A physiological variable decision statistic is formed reflecting the level of the physiological variable. In an embodiment, an alarm indication, such as a patient low-oxygen alert warning, is generated based on processing the physiological variable decision statistic in conjunction with the decision statistic. Information related to the alarm indication, such as a text warning (e.g., "hypoxia/desaturation of patient X in room 102" is provided for presentation to a clinician on a computer output device e.g., a touch pad).

BRIEF DESCRIPTION OF THE DRAWINGS

Embodiments are described in detail below with reference to the attached drawing figures, wherein.

DETAILED DESCRIPTION

Figure 1A:
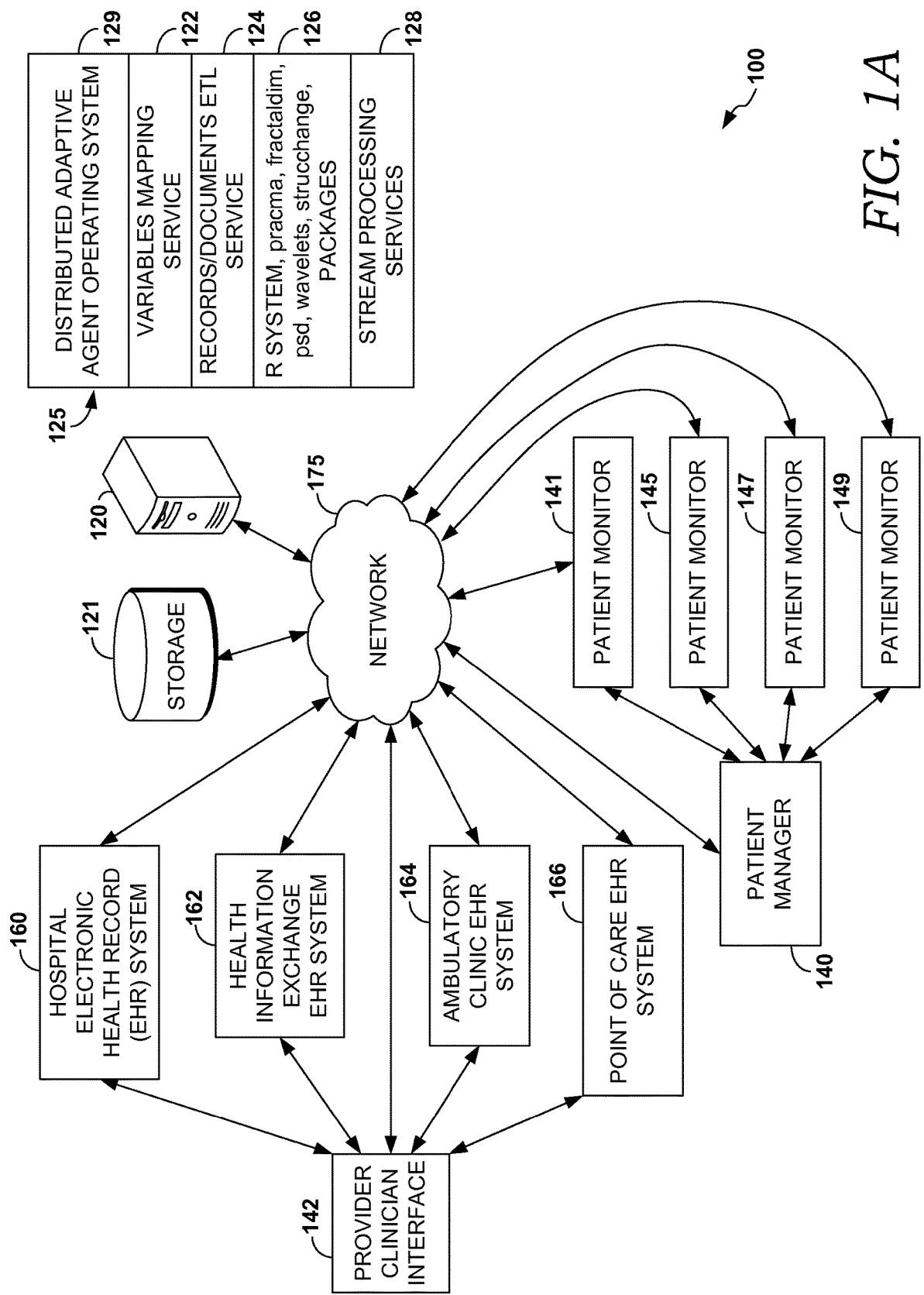
FIGS. 1A, 1B, and 1C depict aspects of an exemplary operating environment suitable to implement embodiments of the present invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

An embodiment is directed to methods and devices for collecting and analyzing data to assess the physiologic status and health of human and/or animal subjects. An embodiment incorporates methods from the fields of digital signal processing (DSP), wavelet spectral analysis, and data analysis of the fractal dimension of a time series signal to detect and ascertain quantitative longitudinal changes in the self-similarity and fractal properties of physiologic time series, reflecting underlying alteration in the functioning of a subject's organ systems. The system and method can serve as a filter to be used in conjunction with monitoring devices' alarm thresholds, for the purpose of reducing the rate of false-alarms emission. Additionally, an embodiment represents a new predictive and classificatory biomarker in its own right and may be used as a basis for (a) asserting alarm conditions worthy of human diagnostic, therapeutic, or preventive intervention or (b) predicting the imminent emergence of such alarm conditions in the near future.

Clinicians in modern acute-care health institutions may be exposed to hundreds of physiologic monitor alarms per patient per day. Monitor alarms are intended to alert clinicians to conditions that may result in harm to the patient. However, when a clinician is faced with an excessive number and frequency of alarms, the disruption and distraction may be so great as to produce so-called 'alarm fatigue', leading the clinician to disregard many of the alarms. This, in turn, gives rise to inferior outcomes, owing to errors of omission and commission.

The problem of alarm hazards is of increasing interest. Such hazards include alarm fatigue and nonresponse, clinically unjustified or inappropriate alteration of alarm settings so as to silence or reduce the frequency of alarm-emission, modifying alarms temporarily without later restoring them to original settings when the circumstances that justified the temporary change have abated, and improper or untimely communication of alarm signals to staff members caring for the patient.

Typically medical device monitors are functionally attached to patients whose clinical condition is sufficiently abnormal as to require such monitoring. As such, true-alarm conditions arise with considerable frequency, often dozens of times per patient-day. Physiologic monitoring devices and their associated alarm thresholds may be designed for high sensitivity, to have a low false-negative rate and to not miss true-alarm events. Concomitantly, a large number of false-alarm conditions also arise each day, resulting in alarms that summon clinicians, in the case when there is no physiological crisis. In addition to high sensitivity, if monitor parameter thresholds are set too tight, true but clinically insignificant alarms arise, known as "nuisance alarms." When alarms are deemed to be "nuisances" (having no clinical import), the clinicians tend to disable, silence, or ignore the alarm warnings. Rather than promoting safety, the net result is to desensitize the users, eroding safety and causing adverse outcomes, such as injury or even death.

False-positive alarm rates and nuisance alarm rates in a clinical setting can be well above 50%. Such high false alarm rates have a negative impact on the clinical decision-making process. Other attempts to minimize false alarms and nuisance alarms have been unsatisfactory in some respects.

An embodiment is directed to a system and method for optimizing physiologic monitoring of a subject, comprising longitudinally measuring one or more physiological variables; constructing a time series from the measurements, de-trending, normalizing, and pre-whitening the series; calculating the fractal dimension of moving-window portions of the resulting transformed time series; applying moving-sum (MOSUM), cumulative-sum (CUSUM), moving-estimate, or other trend analysis test(s); and, if such test(s) indicate a statistically significant transgression of a control limit, or decision statistic threshold, applying signal fusion with conventional physiological variable decision statistic signals such as threshold transgression of the physiological variable value or area-under-the-curve (AUC) of the physiological variable series transgression.

An embodiment enables reliable determination of true-positive versus false-positive alarms, substantially reducing so-called "alarm fatigue" associated with the emission of false-alarms. This may provide a more effective means of mitigating health risks associated with excessive false alarming, compared to other efforts that rely solely on time-series analysis or simple threshold transgression.

An alarm generation system should provide decision input criteria that allow the system to detect a very high fraction of life-threatening situations that require prompt attention, (should have a low false-negative rate). Additionally an alarm generation system should ascertain dangerous situations quickly. Further, an alarm generation system should have a very low rate of false-positives, (indicating a hazard when none exists). In other words, the statistical sensitivity and specificity should both be as high as possible, preferably close to 100%. Beyond this, some monitoring device alarms may have one or more of the following goals: (1) Suppression of alarm emission in situations that are not threatening or whose severity does not require prompt attention; (2) Diagnostic and classificatory alarms denoting a pattern or predicate that merits a particular type of therapeutic attention or intervention, as opposed to merely disclosing an out-of-range condition; and (3) Detection of sensor or device malfunction, so that appropriate maintenance or corrective action can be undertaken to restore accurate and physiologically valid sensor measurements.

Some efforts attempt to decrease false-positive alarms and increase the statistical positive predictive value (PPV) of alarms that are emitted by physiological monitoring systems. Alarm filtering that is based on time integrals or area-under-the-curve (AUC) for persistent excursions of a physiologic signal outside of the alarm threshold provide some benefit insofar as transient threshold transgressions often do tend to self-correct. Adding short delays of up to about 120 seconds may significantly decrease the number of false-positive alarms. Some approaches may use signal morphology, timing differences, cross-correlation between two or more signals, signal rate-of-change, or signal-to-noise ratio or other signal quality metrics to improve alarm accuracy.

Other attempts or efforts at decreasing false alarm conditions are deficient due to:

(1) Excessive false-positive "false-alarm" rate, especially for hypoxia/desaturation or bradycardia or tachycardia or ventricular fibrillation;

(2) Excessive false-negative rate, especially for ventricular tachycardia and similar conditions;

(3) Delays of up to 120 seconds or more after threshold transgression when a signal is longitudinally observed or summed (AUC) to determine whether persistence of the signal's abnormal out-of-bounds state qualifies for notifying the clinician of the alarm conditions;

(4) Arbitrary factory-preset default alarm thresholds that are not context-sensitive to the particular attributes and physiological variable time series distribution or frequency-domain power spectrum of signals arising in a particular patient or population of patients;

(5) Proneness to arbitrary resetting of user-adjustable thresholds, so as to silence alarms or reduce the rate or likelihood of alarms being emitted. Doing this generally entails arbitrarily permitting commensurate increase in a false-negative rate, suppressing true alarm conditions warranting attention and preventive/corrective action;

(6) Necessity of using multivariate signals that relate to two more physiological variables, often from two or more sensors, which may entail extra expense, and involve difficulties assuring non-skewed time coordinates from the data-feeds from multiple data acquisition systems;

(7) Process complexity that entails extra preparation and ongoing work for the clinician, and a higher level of training required for the clinician to use the system properly;

(8) Process complexity involving k-nearest neighbor (k-NN), support vector machine (SVM), neural network, Bayesian, or other clustering and decision-tree induction algorithms to establish thresholds and methods for discriminating 'normal' from 'abnormal', alarm-worthy states;

(9) Static control-limit thresholds and algorithms, such that individualization to particular disease-states or personalization to particular patients is not practical;

(10) The need for a user to know the patient's diagnoses or clinical context and be able at the outset to select exactly one diagnosis or context descriptor that best characterizes the population to which the relevant control-limits or algorithms or alarm thresholds are to be localized. Frequently patients have multiple concurrent/comorbid diagnoses, such that selecting one context diagnosis is difficult or invalid to do, since there are several that would simultaneously be applicable. But if a combination of conditions is chosen as a baseline, there may not be sufficient prior data to guide threshold estimation or selection. Other patients who have not yet received a diagnosis or diagnoses established at other health institutions are not available or known to the user, such that selecting an alarm-localizing diagnosis is not possible at the time that measurements and physiologic monitoring commence; and

(11) Lack of automatic adaptation to the longitudinally evolving context or physiologic condition of the patient, so that patient diagnosis must be changed or updated with the passage of time.

An embodiment uses one or more of the following: (a) one or more of de-trending, demeaning, normalization and pre-whitening of a timeseries, potentially removing the effects of drift, location and scale; (b) calculating a fractal dimension of a time series for a subset, or segment of the time series; (c) calculating an aggregating statistic from a sequence of fractal dimension estimates using one of a trend statistic, a moving sum, a cumulative sum, a moving estimate, and an F-test to determine whether recent fractal dimension values depart in a meaningful statistical way from a baseline; (d) emitting an alarm if the aggregating statistic of fractal dimension departs from a baseline breakpoint threshold limit and a physiological variable decision statistic, (such as a physiological variable level, moving window estimate, trend estimate) formed the physiological variable time series departs from a physiological variable threshold limit. In an embodiment, no alarm is emitted even when a physiological variable decision statistic is out of bounds of a physiological variable threshold, if an aggregating statistic does not depart from a baseline dimension breakpoint threshold limit. In an embodiment, a maintenance indication is emitted when a physiological variable decision statistic is out of bounds, but a physiological variable dimension decision statistic is not out of bounds.

An embodiment automatically personalizes an alarm for monitored Pulse Oximetry. A series of patient pulse oximetry data was acquired, taken from fingertip plethysmographic $SpO_2$ data provisioned with a 0.5 Hz sampling rate and ±1% precision and accuracy. Recorders were randomly selected from a patient health records data warehouse, which is derived from Cerner electronic health record (EHR) from 100% of episodes of care that are incident upon the participating health institutions. The personally identifiable information was removed in conformance with U.S. HIPAA law and regulations, and the de-identified data were stored in a separate, secure database. An embodiment was able to identify positive alarm signals with 98% sensitivity and 99% specificity. The false-positive false-alarm rate in the derivation cohort was 2.4%, a 95% reduction compared to the historical control cohort (48%, p<0.001) with the lower alarm limit set at SpO2=89%. The false-negative true-alarm suppression rate was 0%. In many cases, the FD-based MOSUM-based detection method was predictive of impending true-alarm conditions up to about 20 samples in advance of actual alarm threshold transgression on the monitoring device itself. This affords a modest amount of incremental time advantage, which may prove valuable with regard to improved patient outcomes and safety.

Turning now to FIG. 1A, there is presented an example operating environment 100 suitable for practicing embodiments of the invention. Example operating environment 100 includes a computerized system for compiling and/or running an embodiment of an information architecture that performs decision support recommendation service. With reference to FIG. 1A, one or more electronic health record (EHR) systems, such as hospital EHR system 160, health information exchange EHR system 162, ambulatory clinic EHR system 164, point of care EHR system 166 are communicatively coupled to network 175, which is communicatively coupled to computer system 120. In an embodiment, components of operating environment 100 that are shown as distinct components may be embodied as part of or within other components of environment 100. For example, the one or more EHR systems 160-166 may be implemented in computer system 120. Similarly, a single EHR system may perform functions for two or more of the example EHR systems shown in FIG. 1A.

In an embodiment, network 175 includes the Internet, and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In an embodiment, operating environment 100 may include a firewall (not shown) between a first component and network 175. In such an embodiment, the firewall may reside on a second component located between the first component and network 175, such as on a server (not shown), or reside on another component within network 175, or may reside on or as part of the first component.

An embodiment of electronic health record (EHR) systems 160, 162, 164, and 166 includes one or more data stores of health records, which may be stored on storage 121, and may further include one or more computers or servers that facilitate the storing and retrieval of the health records. In an embodiment, one or more EHR systems 160, 162, 164, and 166 are implemented as a cloud-based platform or are distributed across multiple physical locations. EHR systems 160, 162, 164, and 166 may further include record systems, which store real-time or near real-time patient (or user) information, such as wearable, bedside, or in-home patient monitors, for example.

Although FIG. 1A depicts multiple example EHR systems, it is contemplated that an embodiment employs only one EHR system, or alternatively, relies on user manager 140 and/or monitor 141 for storing and retrieving patient record information such as information acquired from monitor 141.

Example operating environment 100 further includes provider clinician interface 142 communicatively coupled to the one or more SHRs 160, 162, 164, and 166. Although environment 100 depicts a direct communicative coupling between interface 142 and the one or more SHRs 160, 162, 164, and 166, it is contemplated that an embodiment of interface 142 is communicatively coupled to the SHRs through network 175. An embodiment of interface 142 takes the form of a user interface operated by a software application or set of applications on a client computing device such as a personal computer, laptop, smartphone, or tablet computing device. In an embodiment, the application includes the PowerChart® software, manufactured by Cerner Corporation. In an embodiment, the application is a Web-based application or applet. A provider clinician application facilitates accessing and receiving information from a user or health-care provider about a specific patient or set of patients for which sleep architecture characterization is to be performed and facilitates the display of results, recommendations or orders, for example. In an embodiment, interface 142 also facilitates receiving orders for the patient from the clinician/user, based on the results of monitoring. In an embodiment, interface 142 is used to display patient condition-information such as illustratively provided in FIGS. 3-5. Additionally, interface 142 may be used for providing diagnostic services, such as evaluating information as discussed in connection to FIG. 2 and FIG. 3.

Example operating environment 100 further includes computer system 120, which may take the form of a server, which is communicatively coupled through network 175 to EHR systems 160, 162, 164, and 166, storage 121, and patient manager 140.

An embodiment of patient manager 140 takes the form of a user interface and application, which may be embodied as a software application operating on one or more mobile computing devices, tablets, smartphones, front-end terminals in communication with back-end computing systems, laptops or other computing devices. In an embodiment, manager 140 includes a Web-based application or set of applications usable to manage user services provided by an embodiment of the invention. For example, in an embodiment, manager 140 facilitates processing, interpreting, accessing, storing, retrieving, and communicating information acquired from monitor 141. In an embodiment, manager 140 is used to display user (or patient) sleep information such as illustratively provided in FIGS. 3-5. In an embodiment, manager 140 sends an alarm indication via network 175 to provider clinician interface 142. In an embodiment manager 140 sends a maintenance indication to provider clinician interface 142. Similarly, a clinician is provided alarm or maintenance information by patient manager 140 or from a monitor (e.g., monitor 141, 143, 144, 145, 146, 147, 148, or 149). Moreover, in an embodiment of manager 140, an interface component may be used to facilitate access by a user to functions or information on monitor 141, such as operational settings or parameters, user identification, user data stored on monitor 141, and diagnostic services or firmware updates for monitor 141, for example.

As shown in example environment 100, manager 140 in an embodiment is communicatively coupled to monitor 141 and to network 175. In an embodiment patient monitor 141, communicates via network 175 to computer 120 and/or provider clinician interface 142. An embodiment of monitor 141 comprises one or more sensor components operable to acquire biometric information about a patient, such as information associated with a particular physical or mental state of the user, and which may be acquired periodically or as one or more time series. In an embodiment, monitor 145 comprises a sensor or probe component operable for sensing a patient's temporal activity, such as sensing EEG signals derived from a patient.

Figure 1B:
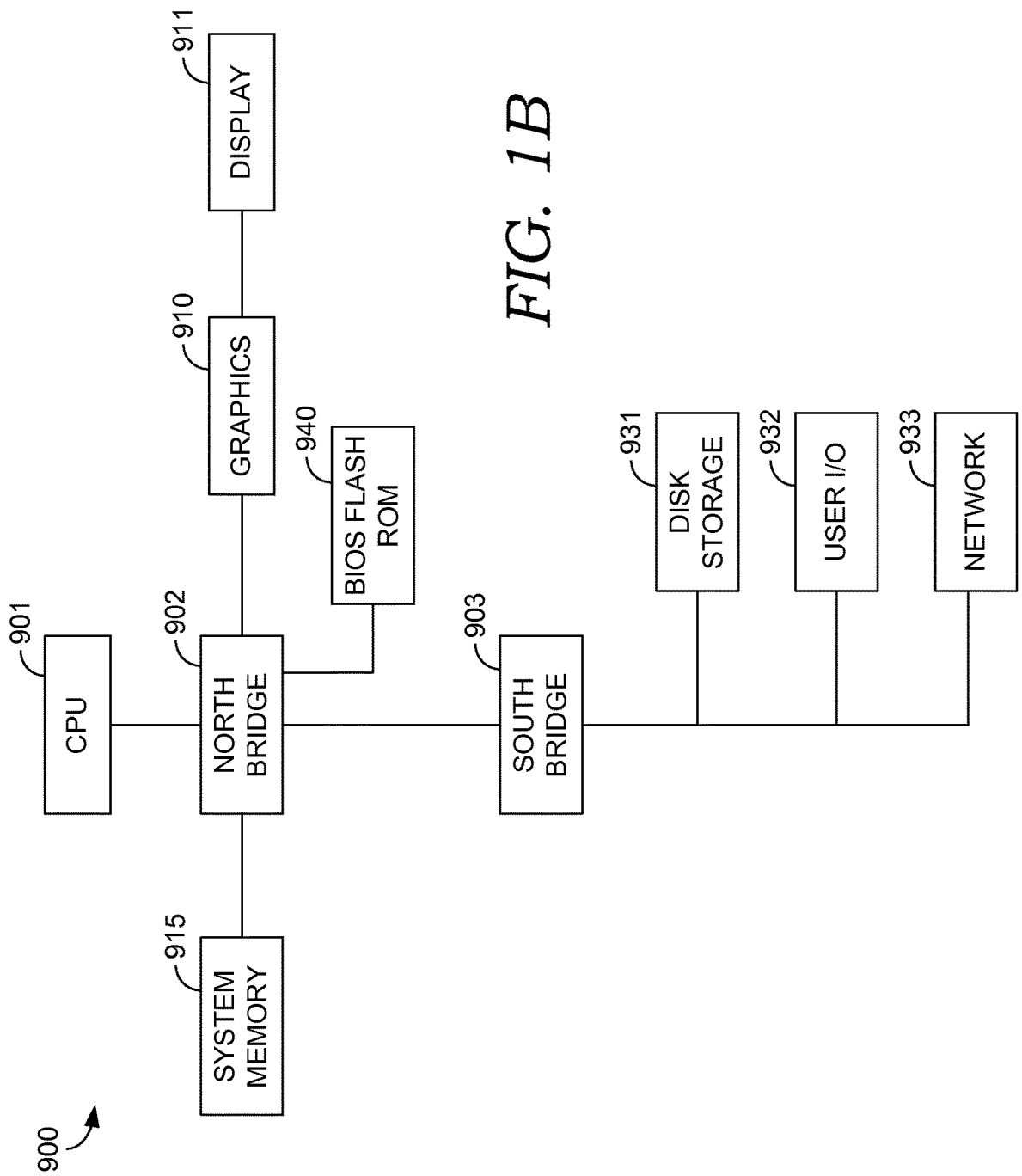
Figure 1C:
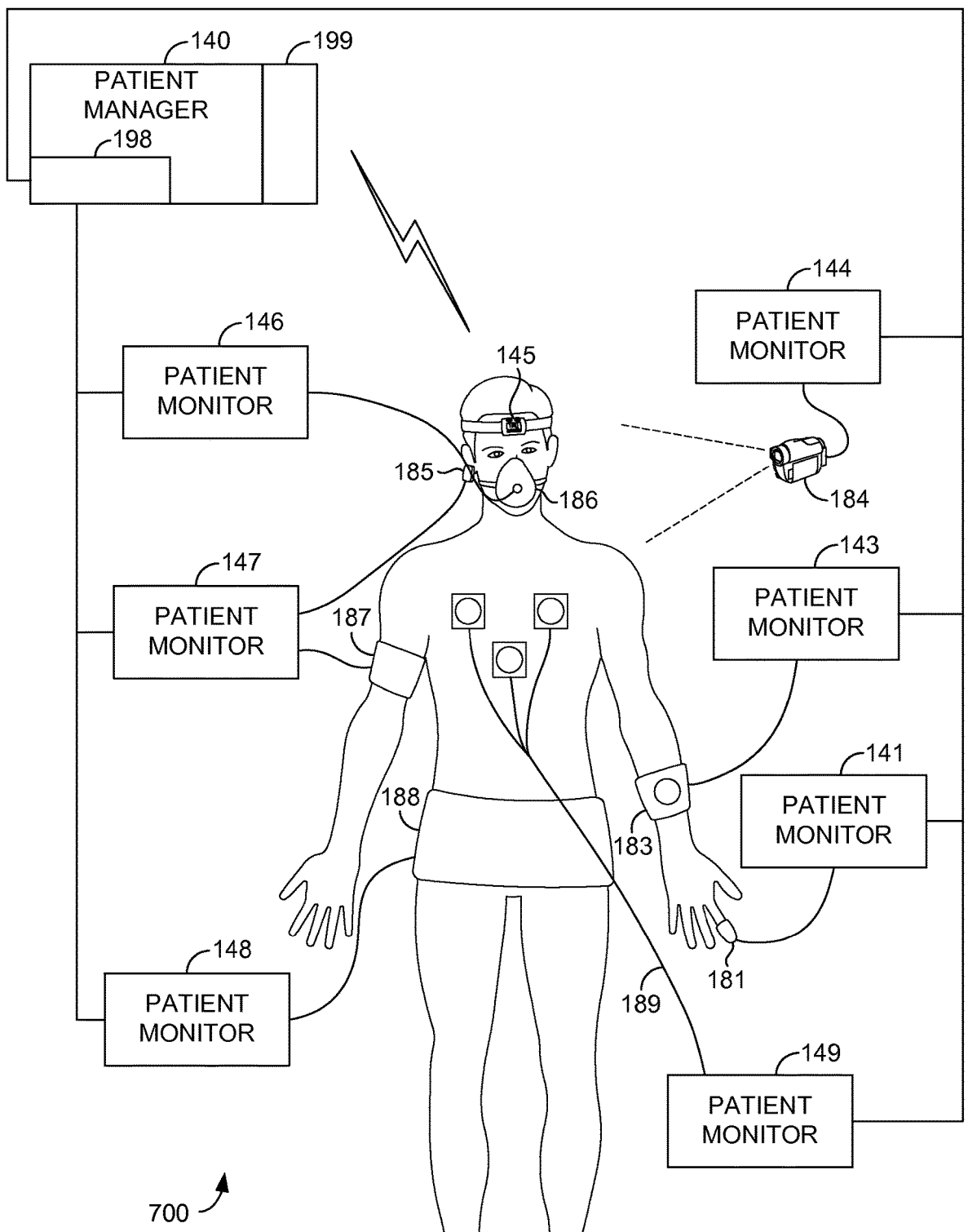

Turning briefly to FIG. 1C, patient physiological variable context diagram 700 illustrates a number of patient monitors (141, 143, 144, 145, 146, 147, 148 and 149) for sensing various types of physiological measurements or physiological variables. A monitor such as 145 may monitor muscle activity, which might be sensed from electromyogram signals, eye movement, which might be sensed from electrooculogram signals, or other biometric information. In an embodiment a monitor such as 145 simply consists of a sensor probe, such as an EEG probe, and a communication link that periodically transmits identification information and probe data to a network interface 199 on a computer such as patient manager 140, so that the time series of monitored values is stored on patient manager 140, enabling the patient manager to form a dimension decision statistic and/or a physiological variable decision statistic. In an embodiment patient monitor 144 collects raw sensor information such as optical sensor 184, and performs signal processing such as movement detection, kinematic modeling, distance and shape processing, velocity measurement, forming an estimate of a dimension parameter, providing a decision statistic based on a dimension parameter estimate, forming a physiological variable decision statistic, fractal dimension estimation, roughness dimension estimation, cumulative summing, trending, wavelet processing, thresholding, computational processing of decision statistics, logical processing of decision statistics, etc. In an embodiment, a monitor such as patient monitor 149, 148, 147, 146, 144, 143, or 141 communicates with a patient manager 140 through wired or wireless network interface 198, thus allowing patient manager 188 to perform multi-sensor or single-sensor processing. In an embodiment a monitor such as 141 makes use of a fingertip oximetry probe 181, to collect data that alarms on condition of hypotaxia/desaturation. In an embodiment, monitor 147 makes use of a first physiological variable probe such as pressure cuff 187 and a second physiological variable probe such as earlobe oximetry probe 185. Probe 187 is useful for irregularities in blood pressure such as unusually high or low mean arterial pressure, diastolic pressure or systolic pressure. Though monitor 147 is shown with two probe types, an embodiment of monitor 147 has an arbitrarily large number of probes for the same physiological variable or for many physiological variables. In an embodiment, monitor 149 makes use of multi-sensor electrocardiogram probe 189. Probe 189 is useful for simultaneously measuring electrical activity of the heart, and respiration rate for detection of bradycardia, tachycardia, ventricular fibrillation, etc. In an embodiment probe 189 is used to detect respiration rate redundantly over three pairs of electrodes, allowing monitor 149 to collect data for detection of hyperventilation, hypoventilation, etc. An embodiment of a probe such as probe 189 monitors one or more of Pulmonary Capilary Web Pressure (PCWP), Left Atrium Pressure (LAP), Central Venous Pressure (CVP), Intra Cranial Pressure (ICP), Central Venous Oxygen Saturation (SCVO2), Hemoglobin Oxygen Saturation (SO2), Arterial Oxygen Saturation (SpO2), temperature, blood pressure, rate, temperature, or other physiological variable. An embodiment of monitor 148 tracks contractions and in-utero baby heart rate for a female subject during labor using cardiotocometer probe 188. An embodiment of probe 188 monitors two patients who are linked e.g., during birth or in a transplant operation. An embodiment of monitor 146 tracks respiration directly through respiration probe 186. An embodiment of monitor 143 tracks temperature with surface temperature probe 183.

In an embodiment, one or more sensor components of monitor 145 may comprise a user-wearable sensor component or sensor component integrated into the user's or patient's living environment. Examples of sensor components of monitor 145 include a sensor positioned on an appendage (on or near the user's head, attached to the user's clothing, worn around the user's head, neck, leg, arm, wrist, ankle, finger, etc.); skin-patch sensor; ingestible or subdermal sensor; or sensor component(s) integrated into the user's living environment (including the bed, pillow, or bathroom); and sensors operable with or through a smart phone carried by the user, for example.

An embodiment of monitor 141 stores user-derived data locally or communicates data over network 175 to be stored remotely. In an embodiment, manager 140 is wirelessly communicatively coupled to monitor 145. Manager 140 may also be embodied as a software application or app operating on a user's mobile device. In an embodiment, manager 140 and monitor 141 are functional components of the same device, such as a device comprising a sensor and a user interface. In an embodiment, manager 140 is embodied as a base station, which may also include functionality for charging monitor 141 or downloading information from monitor 141.

Additionally, an embodiment of monitor 145 shown in FIG. 1C includes some functionality of manager 140. For example, an embodiment of monitor 145 includes a user interface with functionality for configuring operational settings, such as on and off or settings for storing and/or communicating sleep-related information acquired from the user information, such as uploading the information to manager 140 or to storage 121, and display functionality for viewing or reviewing physiological variable information acquired from a patient. In one embodiment, monitor 145 is embodied as a Zeo™ sleep sensor headband manufactured by Zeo Inc. of Newton, Mass.

With reference to FIG. 1A, an embodiment of monitor 145 includes analog-to-digital (A/D) converters for converting analog-acquired information into digital information. For example, in one embodiment, user information is acquired at 512 samples per second. Because sleeping-related signals include low frequencies in comparison to other biological signals, an appropriate sampling rate is determined to adequately capture information sufficient to characterize a user's sleep architecture. For example, Delta or Theta cycles have comparatively low frequencies.

In an embodiment, monitor 145 includes functionality for processing user-derived information locally or for communicating the information to computer system 120 or manager 140, where it may be processed. In an embodiment, the processing may be carried out or facilitated by one or more software agents, as described below. In an embodiment, the processing functionality, which may occur on monitor 141, manager 140 and/or computer system 120, includes signal conditioning, such as removing noise or erroneous information. In an embodiment processing functionality is operable to process user-derived information, such as EEG waveform data, as it is acquired, continuously or periodically such as every 10, 15, 30, or 60 seconds or every few minutes. In an embodiment, the processing includes classifying the user-derived information acquired for a particular time interval into a category. For example, in an embodiment, monitor 145 samples a user's EEG information and processes (or communicates to manager 140 or computer system 120 for processing) the information approximately every time interval to classify the user's state for that time interval. For example, every 30-second time interval, the user's sleeping state may be determined to be one of stage 1, stage 2, etc., theta, delta, etc., or awake, light sleep, REM sleep, deep sleep, or undetermined. Furthermore, in an embodiment, processing further includes determining a sleep score or sleep number, which qualifies the sleep state. In an embodiment, this sleep score is based on the number of time intervals occurring within the sleep categories for a user over a night. In an embodiment of monitor 145 comprising a Zeo sleep sensor device, described above in connection to FIG. 1C, some models of the Zeo device include functionality for determining a number quantifying the user's sleep based on total sleeping time, and time spent in various sleep states, which is referred to as a ZQ (for Zeo Quotient).

Computer system 120 comprises one or more processors operable to receive instructions and process them accordingly, and may be embodied as a single computing device or multiple computing devices communicatively coupled to each other. In an embodiment, processing actions performed by system 120 are distributed among multiple locations such as one or more local clients and one or more remote servers. In an embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

An embodiment of computer system 120 includes computer software stack 125, which in some embodiments operates in the cloud, as a distributed system on a virtualization layer within computer system 120. An embodiment of software stack 125 includes a distributed adaptive agent operating system 129, which may be implemented as a platform in the cloud, and which is capable of hosting a number of services such as 122, 124, 126, and 128. An embodiment of services 122, 124, 126, and 128 run as a local or distributed stack in the cloud, on one or more personal computers or servers such as system 120, and/or a computing device running manager 140. In an embodiment, manager 140 operates in conjunction with software stack 125.

In an embodiment, variables indexing service 122 and records/documents ETL service 124 provide services that facilitate retrieving frequent item sets, extracting database records, and cleaning the values of variables in records. For example, variables indexing service 122 may perform functions for synonymic discovery, indexing or mapping variables in records, or mapping disparate health systems' ontologies, such as determining that a particular medication frequency of a first record system is the same as another record system. In an embodiment, these services may invoke software services 126. Software services 126 perform statistical software operations, and include statistical calculation packages such as, in an embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including tsDyn or similar services for facilitating implementation of nonlinear autoregressive time series models, pracma for performing practical numerical mathematical functions, fractaldim for estimating fractal dimension, psd for estimating the power spectral density, wavelets for computing wavelets and in some embodiments assisting estimation of fractal dimension, strucchange for testing monitoring and dating structural change, tseriesChaos for nonlinear time series operations, or arulesSequences or similar services for facilitating operations such as K-nearest neighbor distance calculations. Software packages 126 are associated with services 128, which include IBM infosphere stream processing services, Apache Hadoop and H base framework, or similar frameworks operable for providing a distributed file system, and which in some embodiments facilitate or provide access to cloud-based services such as those provided by Cerner Healthe Intent®.

Example operating environment 100 also includes storage (or data store) 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health-care provider information, for example. It is contemplated that the term data includes any information that can be stored in a computer-storage device or system, such as user-derived data, computer usable instructions, software applications, or other information. In an embodiment, data store 121 comprises the data stores associated with the one or more EHR systems, such as 161, 162, 164, and 166 and patient manager 140. Further, although depicted as a single storage data store, data store 121 may comprise one or more data stores, or may be in the cloud.

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in an embodiment, computer system 120 is a computing system made up of one or more computing devices. In an embodiment, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In an embodiment, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2A:
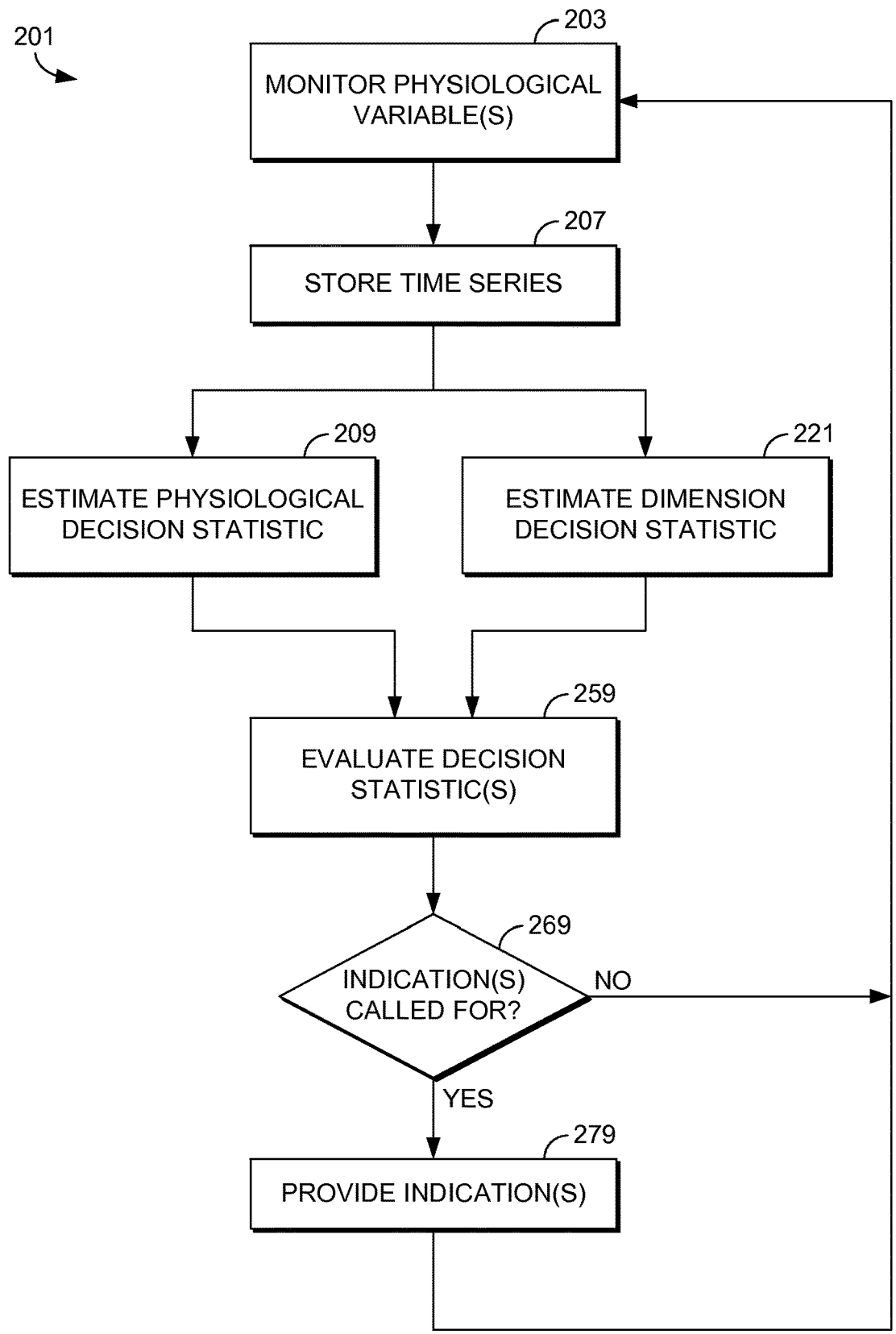
FIGS. 2A and 2B depict a flow diagram of methods of clinical decision processing, in accordance with embodiments of the present invention.

FIG. 2A presents a general flow diagram of a method 201 of clinical decision-making for a computer to decide, based on physiological variable data, whether or not to provide an indication to a user of a physiological variable event such as an alarm or a maintenance notification. At 203, one or more physiological variables are monitored for a patient. In an embodiment monitoring involves sensing one or more physiological variable values, recording successive values into a time series, and performing preliminary processing on the time series to put the data into a regular state and/or scale and/or format. In an embodiment pre-processing includes de-trending, de-meaning, and pre-whitening. At 207 the time series is stored (e.g., within patient monitor 141, patient manager 140, or storage 121). At 221 a dimension decision statistic is formed from an estimate of one or more dimension parameters. In an embodiment a dimension parameter is roughness. In an embodiment a dimension parameter is fractal dimension. The dimension decision statistic is calculated from the dimension parameter, e.g. by forming a moving sum or cumulative sum over the time series. In an embodiment, at 209 a physiological decision statistic is formed. A physiological decision statistic is one that provides a value related to a physiological variable to be considered. For example, the predicted SpO2 level such as 90% for a trend that is three seconds into the future based on the last five seconds of data is an example of a physiological decision statistic. At 259 The dimension decision statistic and/or the physiological decision statistic are evaluated to make a clinical decision. In an embodiment the evaluation performs a function that is logical and/or numerical to provide input for a resultant one or more computerized actions. For example, if the physiological decision statistic indicates a value above a threshold, e.g. 93%, and if the dimension decision statistic is above a dimension breakpoint level, then an alarm condition is generated and at 279 an indication is provided by a computer module to another computer module for resultant action. In an embodiment, a maintenance condition is generated at 259 if the physiological decision statistic is below a threshold value, and if the dimension decision statistic is below a breakpoint threshold. In an embodiment the dimension decision statistic is evaluated, and if it is above a breakpoint threshold, an alarm condition is generated. At 269 a decision is made as to whether or not one or more indications are called for due to the presence of one or more conditions that have been determined at 259, such as alarm conditions or maintentance conditions. If no underlying condition is present necessitating that an indication be generated, the method proceeds to 203. If an underlying condition is present, the method proceeds to 279 where one or more appropriate indications are provided. In an embodiment, an alarm condition results in a software module indicating to a receiving software module that the dimensionality of the physiological variable is in an unsafe region. In an embodiment, patient context is drawn from storage such as that in patient manager 140 and the current values of patient data are extracted and presented to a clinician together with a display or announcement of an alarm condition such as "danger patient is likely blue, tissue damage imminent." From 279, the method returns to 203 to provide additional data and/or evaluation for a monitored patient.

Figure 2B:
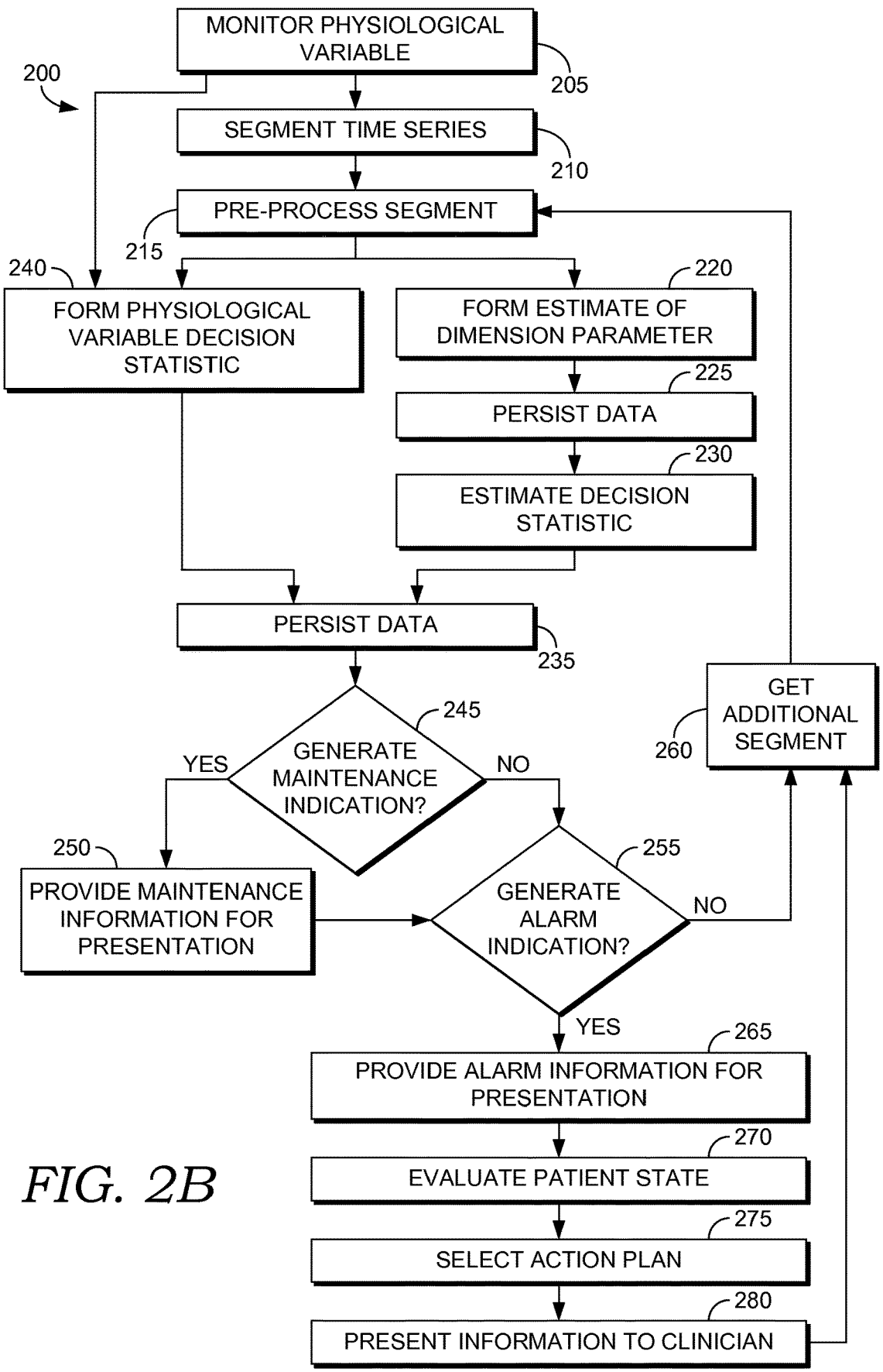

Turning now to FIG. 2B, a flow diagram is provided for an embodiment of a method 200 of clinical decision-making describing how physiological variable data is interpreted by a computer to decide whether or not to indicate within computer storage the existence of an alarm region or a maintenance region based on one or more decision statistics formed from physiological variable data. In an embodiment, once an alarm or maintenance region is indicated within computer storage, information related to the decision region such as diagnostic services information or an evaluation of the context of the region to patient care is presented to a clinician, e.g. on a provider clinician interface 142.

At 205 one or more physiological variables of a patient are monitored. In an embodiment a single physiological parameter such as SpO2 is collected from a patient. In an embodiment a vector of physiological variables are monitored, such as those discussed in conjunction with FIG. 1C. As time continues, the monitored physiological variables form a time series describing each physiological variable level at an associated sequence of time instants. In an embodiment the values of the one or more resulting time series are buffered within a monitor such as 149, a patient manager 140, a computer 120 or network storage 121. The one or more physiological variable time series may be considered as a collection of raw data reflecting source physiological parameters of interest. In an embodiment, the monitoring at 205 collects the raw data of SpO2 every half second and buffers the resulting information for further processing.

At 210 one or more time series of the one or more physiological variables are segmented. In an embodiment, a scalar physiological variable such as SpO2 makes use of a segment of samples such as 7, 40, 50, or 60 samples, corresponding to 3.5 sec., 20 sec., 25 sec., and 30 sec., respectively. In an embodiment, a time series of physiological variable values is up-sampled or interpolated to a higher time-resolution standard time scale such as 0.1 sec. In an embodiment, a time series of physiological variable values is down-sampled to put the time series on a more coarse time interval, e.g. by taking every fourth sample to give four parallel segments of data points every 2 seconds, or by producing a single segment every 2 seconds by averaging four adjacent physiological variable values thus reducing the rate of data by ¼. In an embodiment all monitored physiological variables are put on a common time scale by a combination of selecting a segment of contiguous samples, down-sampling, or up-sampling. In an embodiment, a segment length for a computation is defined, but additional data are buffered added to a computational segment and processed to provide a stream of computations at the segment length.

In an embodiment, at 215 a segment is pre-processed to put data on a common footing and/or to prepare segmented data for statistical processing. In an embodiment, a very small fixed or random number is added to each data value in a segment, to prevent down-line analyses from becoming numerically unstable. In an embodiment, pre-processing includes de-trending and de-meaning a time series segment. In an embodiment, pre-processing includes whitening the time series segment. In an embodiment, whitening involves treating a scalar segment as a vector and pre-multiplying an input vector by the square root of the eigenvalue matrix, and pre-multiplying the result by the eigenvector matrix. In an embodiment, data is normalized to put the resultant time series data on a common scale (e.g., zero to one) for ease of comparison between use cases.

At 220 an estimate is formed of one or more dimension parameters. A dimension parameter is a parameter that reflects the dimension (or degree) of roughness and/or the fractal dimension of the underlying time series. In an embodiment a scalar dimension parameter is estimated from a scalar-valued physiological variable for a segment of the time series. In an embodiment, a fractal dimension is estimated from a vector comprising two or more physiological variables for a segment of a time series. In an embodiment a vector of dimension parameters is estimated from a vector of physiological variable values over a time series, so that each element of the output estimated vector is formed from the corresponding physiological variable value in an input vector. In an embodiment, a scalar value dimension parameter is estimated from an input vector of physiological variables, so that all physiological variables in the vector contribute to the dimension estimate. In an embodiment, a scalar fractal dimension is estimated from a scalar-valued physiological variable for a segment of a time series. Fractal dimension is an expression of the self-similarity of a spatial or temporal object. In an embodiment, statistical software routines such as the R Modules pracma, fractaldim, wavelets, and strucchange perform the estimation. In an embodiment, a fractal dimension parameter is estimated by using wavelet transformation, Higuchi, Katz, K-Nearest Neighbor, rescaled-range (R/S), autocovariance function (ACVF), Whittle, Hall-Wood, box-count, Discrete Cosine Transform, Variogram or Cevcik methods.

A roughness dimension parameter is a statistic that quantifies the degree (or dimension) of phase reverses and/or the magnitude of phase reverses in an underlying segment. Examples of roughness parameters include: the arc length of a segment of scalar values, the surface area of a segment of vector values, the approximate arc length of a best fit line approximating a scalar time series, an absolute difference statistic for a defined lag, a second order difference statistic for two different defined lags, and one or more of the roughness statistics defined for segment size K below as R1(X,L), R2(X), and R3(X,i,j).

$$R1(X, L) = \frac{1}{K-L} \sum_{m=1}^{K-L} |X_m - X_{m+L}|$$

$$R2(X) = C_1 - C_2(\log(R1(X, 2)) - C_3\log(R1(X, 1)))$$

$$R3(X, i, j) = C_1 - \frac{C_2 R1(X, i) - C_3 R1(X, j)}{\mu_K}$$

$$\mu_K = \frac{C_4}{K} \sum_{m=1}^{K} X_m$$

Note that m is a time sample index, X is a scalar or a vector of one or more physiological variable values, K is the segment length. In the definition of R1(X,L) for the scalar case the operator shown is absolute value, but it is contemplated that for the vector case the operator is replaced by p-norm, sup-norm, frobenius-norm, 1-norm, 2-norm, L-norm, or infinity-norm instead. In general the scalar constants $C_1$, $C_2$, $C_3$, and $C_4$ are suggested to be positive values but could also be any combination of positive and negative values.

At 225 the estimated data is persisted so that one or more estimate results from prior segments are also available to the estimate of a decision statistic at 230. In whatever way the estimate of the decision statistic is made, a patient monitor e.g. patient 149, a patient manager 140, or a networked computer 120 stores a value in memory as a decision statistic for the present segment, and so provides a decision statistic based on the estimate of dimension parameter that has been formed. In an embodiment, at 230 a trend statistic is formed from the dimension parameter for the present segment and from one or more dimension parameters from prior segments. In an embodiment, at 225 a moving window or first-in-first-out buffer is formed of the estimated dimension parameters over two or more segments. At 230 a trend statistic is formed over a moving window using a technique such as calculation of a moving sum (MOSUM), cumulative sum (CUSUM), a weighted linear combination, a non-linear moving estimate, and an F-Test.

In an embodiment, the segment for estimation is chosen large enough that several subsegments that make up a segment contain a dimension estimate over the window of a subsegment. In an embodiment, one or more dimension parameters for the present segment at 220 provide the decision statistic at 230. In an embodiment, one or more dimension parameters for the present segment are combined mathematically to form an estimate of the decision statistic. For example, a vector of dimension estimates is element-wise compared to a vector of dimension thresholds suitable for each physiological variable element, in conjunction with a vector of physiological variable dimension scale values. The largest difference measured as a fraction of corresponding dimension scale for an element is chosen as the decision statistic.

In an embodiment, at 240 a physiological variable decision statistic is formed. In an embodiment the most recent level of the physiological variable monitored at 205 is taken as a current physiological variable level that forms the physiological variable decision statistic. In an embodiment, at 240 raw physiological variable values are persisted for a time period. In an embodiment, the physiological variable decision statistic is formed based on the segment length and/or values of the pre-processed current segment and/or previous values of pre-processed segments. In an embodiment, a predicted level of the physiological variable, e.g. that provided by a Kalman filter, at a future time is estimated based on persisted data. In an embodiment, a physiological variable decision statistic is formed by one or more of a mathematical function of persisted data, a velocity estimate of physiological variable value, a linear prediction based on persisted data, a truncated taylor series expansion based on persisted data, a physiological variable trend statistic, a recent average value, a median filtered estimate, a rank order filtered estimate, a scaled area under the curve estimate, and a Kalman filter.

In an embodiment, at 245 the method decides whether or not to generate a maintenance indication. In an embodiment, a physiological variable decision statistic is compared to a physiological variable alarm threshold level to determine if the physiological variable decision statistic has crossed into a region of concern. For example, if the physiological variable monitored is SpO2, and the threshold is set to 91%, then a physiological variable decision statistic of 0% as indicated at time mark 288 in FIG. 4, indicates a region of concern, which is low physiological variable value. In another example, if the physiological variable monitored is heart rate, and the threshold is set to 100 beats per minute, then a physiological variable decision statistic of 105 beats per minute indicates a region of concern, which is high physiological variable value, or tachycardia. In an embodiment, the physiological variable threshold is a predetermined level based on the particular physiological variable monitored. For example, an SpO2 threshold level is set at 91% because clinical action should be taken if the patient condition is beginning to drop persistently below this level. In an embodiment, the physiological variable threshold is a dynamic function related to other physiological variables or patient state variable. For example, if a sleep state is indicated by an EEG monitor such as monitor 145, then a bradycardia threshold for a monitor such as 149 is reduced by 10. Similarly, if an agitation state is indicated by the kinematics measured in monitor 144, then a tachycardia threshold for monitor 149 is increased by 25. In an embodiment, the physiological variable threshold level is established when a clinician manipulates a user interface control that sets a stable baseline physiological variable level, and an alarm limit is set as a certain fraction above or below a baseline level.

Figure 5:
FIG. 5 presents a time series of fractal dimension estimate as a function of time for a patient.

In an embodiment, a dimension decision statistic is compared to a breakpoint threshold to determine if the dimension decision statistic has crossed a breakpoint threshold. For example, if the dimension decision statistic is a fractal dimension trend such as an empirical fluctuation process of a moving sum estimate as shown in FIG. 5, with a breakpoint threshold of about 5.6, a moving sum value of 2 at time mark 288 would indicate that the dimension decision statistic is in a region of low dimension. In another case, if the physiological variable dimension decision statistic is generally high at a dimension estimate of 2.1, and a breakpoint threshold is set at 1.5, then a value of 1.4 of the dimension decision statistic would indicate that the dimension decision statistic is below the breakpoint threshold and has entered a region of dangerously low dimension. In an embodiment, one or more breakpoint threshold levels are established when a clinician manipulates a user interface control that sets a stable baseline physiological variable dimension level, and one or more alarm limits are set as a certain fraction above or below a baseline level. In an embodiment the dimension breakpoint threshold is a predetermined level based on the physiological variable monitored. In an embodiment the dimension breakpoint threshold is a level set based on the particular context of care, such as whether or not the monitoring is performed in an Intensive Care Unit, a surgery pre-screening evaluation station, or a post-surgery release screening station. In an embodiment the dimension breakpoint threshold is determined based on the context of other monitored physiological variables. For example, the dimension breakpoint threshold of a respiration rate physiological variable monitor 146 is modified based on the sleep state detected by monitor 145 or based on the kinematic motion state detected by monitor 144.

In an embodiment, at 245 a maintenance indication, such as data indicating a need for maintenance, is generated when a physiological variable decision statistic has crossed an alarm threshold level and a dimension decision statistic has not crossed a dimension breakpoint threshold. For example, in the example depicted in FIGS. 4-5 at time mark of approximately 288, the SpO2 sensor indicates a physiological variable level below 88%. Since the dimension decision statistic is below about 5.6 a maintenance indication is generated because the method has determined that the SpO2 physiological variable decision statistic is less than 88% and therefore below 91%, but the dimension decision statistic is below 5.6, and hence this event is interpreted as a sensor failure of some sort. In an embodiment, at 250 a piece of equipment at patient bedside announces a message "please replace fingertip sensor," allowing the patient himself, or anyone in the room to assist necessary monitoring. In an embodiment, at 250 a maintenance needed record is created. In an embodiment, the record is interpreted and displayed to lower cost clinical staff alerting them to a substandard condition where a patient is not being properly monitored. In an embodiment, the record and display are maintained as long as the patient is continuously monitored and remains in the determined state, but the maintenance condition is removed when the physiological variable returns to an acceptable level for a monitored patient. In an embodiment a maintenance display is generated for maintenance clinical staff showing a list item for the patient, and/or a yellow-flashing room where the lack of monitor condition is present. In an embodiment a tone or verbal annunciator warning is periodically sent to alert maintenance staff to the lack of monitor condition. In an embodiment an indication is presented on a maintenance display alerting clinical staff to an unmonitored condition. In an embodiment a notification is transmitted from a monitor informing clinical staff about the maintenance state. In an embodiment a message is sent from a monitor to a remote computer containing the decision statistic variables and a remote computer evaluates the maintenance condition based on monitor variables and on other monitor variables. In an embodiment, a message is sent from the monitor to a remote computer containing a trigger that generates a maintenance notification by the remote machine for the monitored patient.

At 255 a decision is made whether to generate an alarm indication. In an embodiment, the decision is based upon evaluating a dimension decision statistic relative to a breakpoint threshold to determine whether the dimension decision statistic has crossed a breakpoint threshold. For example, when the dimension decision statistic is above a threshold it is in a first region, but when the dimension decision statistic is below a threshold it is in a second region. In an embodiment, a decision region is an alarm region, a non-alarm region, a maintenance region, a non-maintenance region, a stable region, an unstable region, a dangerous region, a safe region, a low region, a high region, etc. For example, in an embodiment illustrated in FIG. 5, when a MOSUM dimension decision statistic is above 5.6, it is determined that the dimension decision statistic has crossed the breakpoint threshold and entered into a high region, and an unstable region. In an embodiment, an indication of the region of the decision statistic relative to the breakpoint threshold is stored in a sensor 145, in a monitor 149, in a patient manager 140, in network storage 121, or in network computer 120.

In an embodiment, at 255 the dimension decision statistic is evaluated in conjunction with a physiological variable decision statistic, such that a complex decision region may be easily defined by combining the information in both decision statistics. For example, multiple trials may be observed and plotted on a two-dimensional graph, and an arbitrary number of decision regions may be defined by an analyst by defining regions to capture different clusters of joint behavior. The two variables may then be jointly evaluated to determine the decision region. Thus a determination is made whether a decision statistic has crossed a breakpoint threshold defined by the two-dimensional analysis. Likewise, the analysis may be applied to make the determination serially. For example, a table could be created that defines a set of thresholds and regions for the dimension decision statistic at each physiological variable decision statistic value. Thus when a determination is made whether the decision statistic has crossed a breakpoint threshold, the thresholds are read from the table, and the region is determined relative to the regions defined in the table.

Figure 4:
FIG. 4 presents a time series of blood oxygen saturation for a patient.
Figure 6:
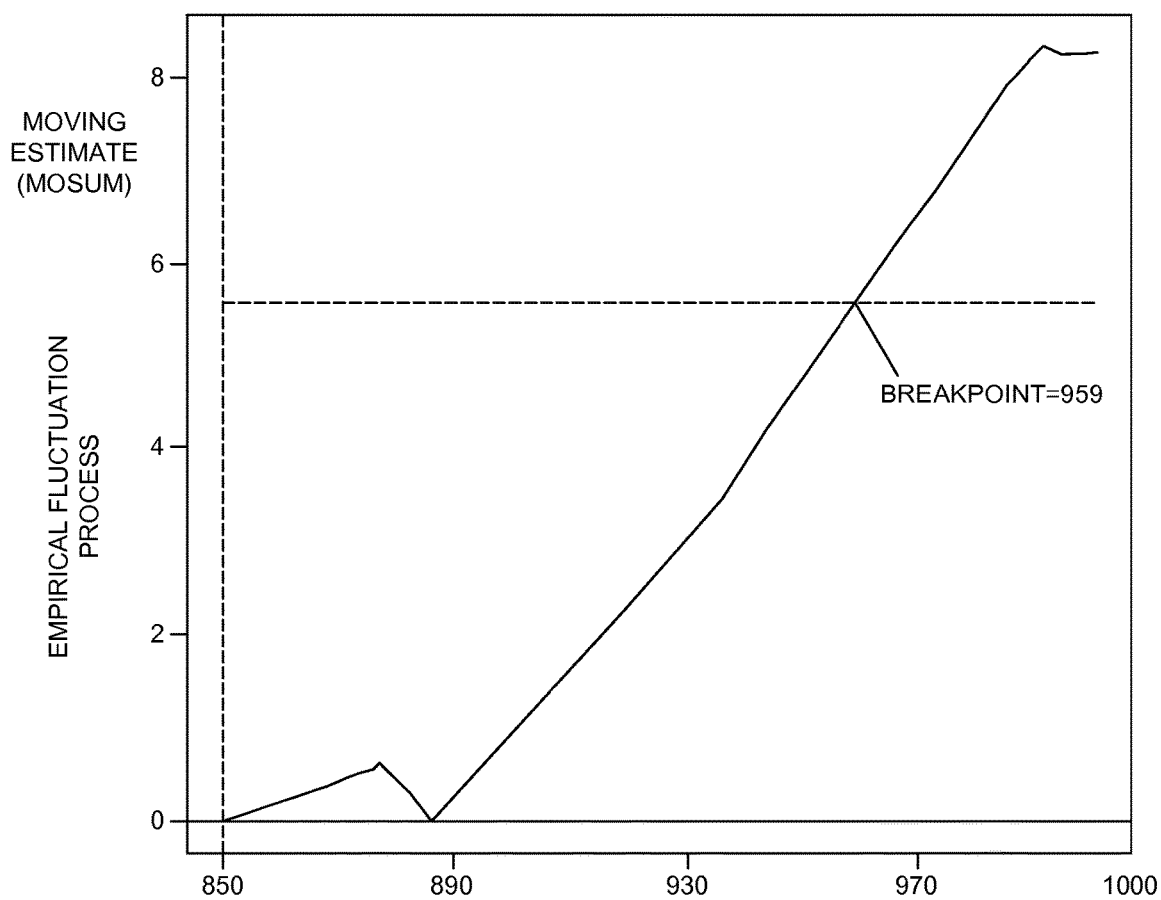
FIG. 6 presents a moving sum estimate used as an empirical fluctuation process for forming a decision statistic for a patient.

In an embodiment, an alarm indication is generated at 255 when the physiological variable dimension statistic is in a particular region and when the physiological variable decision statistic is in a particular region and/or condition. For example, as illustrated in FIGS. 4-6, beyond time mark 959, the method determines that the dimension statistic is above about 5.6, and the physiological variable decision statistic illustrated in FIG. 4 has dropped below 91%, and therefore the method generates data recorded in memory to indicate that an alarm condition is present for the patient. As a second example, also illustrated in part by FIGS. 4-6, an alarm indication is generated when the trend of the physiological variable decision statistic is headed lower at the time the dimension decision statistic crosses into an unstable region, and the present physiological variable level is within a tolerance of the threshold, such as within 2% of the threshold. In an embodiment, based at least in part on a dimension decision statistic, it is determined that the physiological variable is in at least one of a low physiological variable value region, a high physiological variable value region, a low physiological variable velocity region, a high physiological variable velocity region, a safe physiological variable level region, and an unsafe physiological variable level region.

In an embodiment, when an alarm is not generated at 255, the method obtains another segment of the time series at 260 and returns to 215 to begin the segment processing for the new segment. In an embodiment, even when an alarm is generated, and the method proceeds to 265 to process the alarm, the method continues to obtain an additional segment at 260 and continues processing of segments in parallel with steps 265-280 so that current information is available for clinicians who continue to give care to the patient.

At 265 based on the alarm indication generated, information related to the alarm is provided for eventual presentation to a clinician. In an embodiment, the identified region is associated by the method with a particular form of alarm signal to alert the appropriate clinician in the most effective way for the particular region of the alarm. For example, when the dimension of the SpO2 sensor has been determined to be dangerously high one or more of the patient identity, the location of the patient, the region of the dimension statistic, the trend of the dimension statistic, the level of the SpO2 physiological variable, and the trend statistic of the SpO2 physiological variable, are recorded within memory to be provided to a clinician who is alerted to the alarm condition. The method then provides the data necessary to give one or more of a visual text, a visual cue, auditory tone, or a verbal annunciator informs the clinician, such that the clinician is informed that "patient Bob Smith in room 102 has dangerously high dimension of SpO2, current level is 91% and falling." In an embodiment a clinician monitors one or more patients in a population, and simultaneously carries out other work orders, or other necessary tasks, or is attending to other patients, or is on call, and is notified of a generated alarm indication.

An embodiment of an alarm indication is one or more of a record indicating that an alarm region is present, permitting a clinician interface such as interface 142 to present at 280 a particularly modulated warning tone (loudness and interruption rate start at a recognizable level and increase to indicate severity of risk), an annunciator, a visual display of a message, a pop-up window on a computer screen, a banner, contextual vital statistics, a determined patient state, a selected action plan, a sequence of visual displays such as video of a room changing color to red and to black, and/or flashing on a map of the facility, transmitting a notification of an alarm state, sending a text message indicating the alarm state, transmitting a message that triggers another computer or communication system to trigger an alarm state in a remote machine, transmitting a message describing an alarm condition and making a computer record of the existence of an alarm condition, and maintaining a record to indicate current alarm state.

In an embodiment, information provided by the method comprises information related to one or more of: determining the effect of one or more drugs, determining the effect of one or more medical interventions, supporting extubating the patient, suggesting extubating the patient, supporting adjustment of patient therapy, supporting an adjustment to medication, suggesting an adjustment to patient therapy, supporting ventilator settings, suggesting adjusting ventilator settings, weaning the patient off ventilation, suggesting weaning the patient off ventilation, assessing patient status before surgery, assessing patient status during surgery, assessing patient status after surgery, assessing patient status before a medical procedure, assessing patient status during a medical procedure, assessing patient status after a medical procedure, monitoring for air leaks, monitoring for improper ventilation, monitoring exercise, monitoring stress levels, monitoring a medical condition and monitoring disease.

In support of presenting information related to the region to a clinician, at 270 an embodiment evaluates the patient state. In an embodiment, available data such as data from data store 121 that pertains to the patient and/or current physiological variable values of monitored physiological parameters, is collected and fed into an analysis and decision engine such as a decision tree classifier that hypothesizes one or more conditions that may be the underlying cause of available data and/or the current alarm region. In an embodiment, the list of potential causes is presented to the clinician, in an embodiment, presented with estimates of likelihood or severity, or in rank order of likelihood or severity. In an embodiment, the list of possible conditions is pruned based on likelihood, severity, or on sound medical reasoning or protocol to determine a single hypothesis to be presented to a clinician. In an embodiment, redundant probes measure the same physiological variable, and patient state is determined based on evaluating the dimension decision statistic for each probe. For example, the probe that has dimensionality closest to a baseline level is the probe used for reporting the physiological variable level.

In an embodiment, multiple physiological variable decision statistics and/or dimension decision statistics from multiple probes are combined to determine patient state, which in turn, are used to select an action plan as indicated at 275. For example, the method may determine based in part on the dimension decision statistic that monitor 145 credibly indicates that the patient is awake, and monitor 144 credibly indicates that the patient is in a restless or agitated state, and monitor 146 credibly indicates an unusually low respiration rate, and monitor 141 credibly indicates low SpO2; therefore, a diagnostic decision tree hypothesizes tracheal blockage, and the method generates a recommendation to the clinician that a Heimlich maneuver should be attempted first, and then artificial emergency respiration, and if the patient begins to turn blue, an emergency tracheotomy should be performed.

Figure 3:
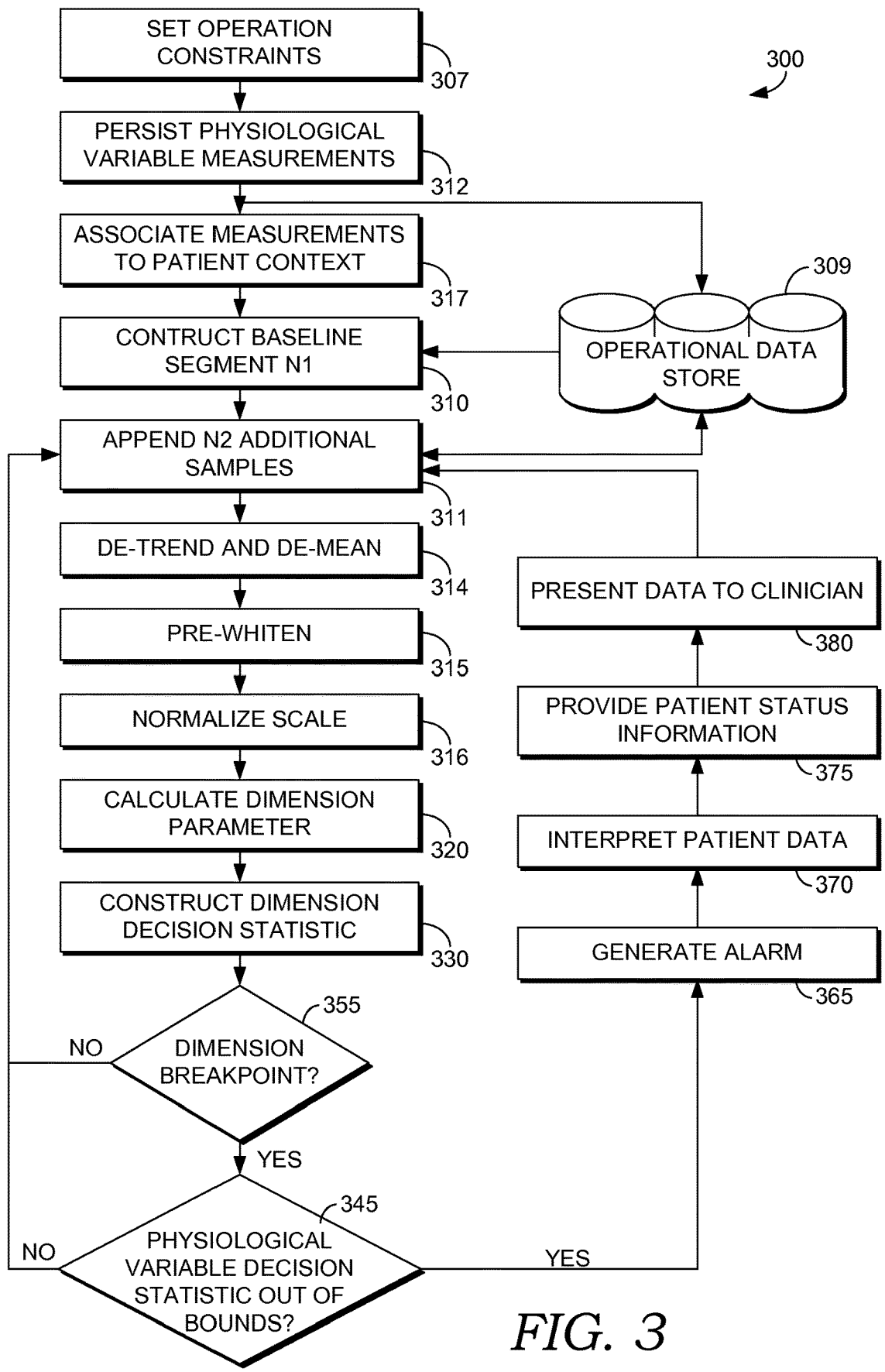
FIG. 3 depicts a flow diagram of an embodiment of clinical decision processing, in accordance with embodiments of the present invention.

Turning now to FIG. 3, there is depicted in 300 a representative flow diagram of clinical decision processing. At 307 operation begins when the equipment is turned on or when a clinician manually resets an alarm, to re-initialize operation. An alarm reset signal in general could be entered by a clinician at any time. In an embodiment, a clinician resets the alarm after being presented with data in 380, so that the operation returns to step 307. At 307, operation constraints for the method are set. In an embodiment a tuple of N1, M, and N2 are selected to constrain the operation of the algorithm. In an embodiment these constants are preset values determined separately for each physiological variable monitored. In an embodiment, a monitor options interface allows a clinician to tune the constraints for the particular application. In an embodiment these constraints are a function of an input operational context such as ICU, in-home, or clinical outpatient setting. In an embodiment, upon alarm reset and/or power up, preset values of N1, M and N2 are used. M indicates the amount of time that will characterize a stable physiology. In an embodiment M is between 7 and 75. In an embodiment M is chosen to be between 40 and 50. N1 is an input that prevents the method of computing fractal dimension from running until there is a long enough time series to run a fractal estimation process. N2 is the number of additional samples that are appended after a fractal dimension test. In an embodiment one or more of N1, M, and N2 are chosen to satisfy one or more of the following constraints: N1>100; 10<M<N1/2; 10<N2<M. There is a trade-off involving stability of the physiology and accuracy of the dimension calculation in the selection of M as large or small. In an embodiment, measurements are accumulated until there are at least N1+M samples and until the coefficient variation falls below a threshold level such as 0.5%. In an embodiment, a monitor emits alarms without a dimensional check on the physiological variable until there is sufficiently stable data of sufficient length to form a dimension estimate. In an embodiment, a clinician initiates dimensionality screening by visually monitoring the patient physiological variables for a stable pattern, and selecting a user interface control that indicates a baseline to initiate screened monitoring.

At 312 physiological variable data is persisted in a manner appropriate to the embodiment, buffering physiological variable data for local processing in monitor 149, sending data to a remote computer 120, or 140 and recording physiological variable data in data store 121. Persisted data is stored in operational data store 309. At 317 a patient identity, and all other patient attributes are associated with the persisted physiological variable data. In an embodiment the physiological variable data is bound to a record of an entity (from a monitoring device or from an electronic medical record.) In an embodiment at 310 data is retrieved from operational store 309 to construct a baseline segment of length N1. In an embodiment, at 311 an additional N2 samples are appended to the segment of the time series analyzed. In an embodiment N2 samples are discarded from the segment analyzed. In an embodiment at 314 a segment of size N1+N2 is analyzed to de-mean and de-trend the samples. In an embodiment of detrending, linear regression is used to calculate a least squares fit to any trend with respect to the time record. This trend is then subtracted from the record. In an embodiment at 315 the time series is pre-whitened. In an embodiment Pre-whitening employs a first-order difference filter (i.e. the value at t−1 is subtracted from the value at t) to remove any low-frequency information from the record. In an embodiment, pre-processing of the time segment includes removing an autogregressive component present in the segment values. In an embodiment, at 316 the time series is normalized, e.g. to put the range of the statistic on a common footing such as a range from zero to one.

At 320 a dimension parameter is calculated for the time series resulting, in an embodiment, in a fractal dimension time series denoted FD(t). In an embodiment each subset of the time series of length M has a moving window computation of the dimension as a function of time. In an embodiment, an empirical fluctuation process (EFP) time series is formed from FD(t). In an embodiment the EFP is calculated by one of a MOSUM, a moving estimate, an F-test, or a trend statistic that detects shift, drift, or changes in dispersion of the FD. At 330 a dimension decision statistic is constructed by, in an embodiment forming a moving window trend analysis of FD(t). In an embodiment the EFP is used as a source of decision statistics. In an embodiment FD(t) is evaluated as compared to a baseline behavior of FD(t). If FD(t) has changed compared to the baseline, it is determined that a concurrent alarm condition should be emitted as an alarm. If FD(t) has not recently changed, then other alarm conditions such as underlying physiological variable alarm conditions are suppressed or censored as long as FD(t) indicates that the dimensionality has not changed recently. At 355 a comparison is made of the constructed dimension decision statistic to a dimension breakpoint. If the dimension decision statistic has not crossed over the breakpoint threshold value, then the method returns to append an additional N2 samples at 311. If the dimension decision statistic has crossed over a breakpoint threshold, then an additional comparison is made at 345 to see if a physiological variable decision statistic is out of bounds. If the physiological variable decision statistic is not out of bounds, then the method returns to append N2 additional samples at 311.

In an embodiment, if both the dimension decision statistic has crossed over a dimension breakpoint and the physiological variable decision statistic is out of bounds, then the method proceeds to generate an alarm at 365. In an embodiment, after a clinician is notified of the alarm generation, and after the cause of the alarm has been addressed the alarm is reset and the method proceeds to 370. At 370 patient data is interpreted to determine the meaning and/or potential cause of the alarm. At 375 patient status information such as vital statistics and alarm context is prepared at 380 this information is presented to a clinician, whereupon the method proceeds to 311 to continue monitoring of the patient by appending N2 additional samples to the time series.

An embodiment was reduced to practice using a computer running the Linux operating system, the open-source statistical software package R, and the R modules pracma, fractaldim, wavelets, and strucchange. Stream processing of the accruing time series was accomplished using IBM InfoSphere Streams' stream-processing software. A cloud-based computing configuration is one alternative embodiment. In an embodiment, a stand-alone server or other computing device equipped with suitable connectivity to the device(s) by which the time series are acquired may likewise be utilized.

The term 'fractal' can be used to characterize spatial objects or temporal time series patterns that show a form of self-similarity over multiple powers of ten in spatial or temporal scale. A fractal is an entity comprised of parts that are themselves 'similar' in structure to the whole entity. The fractal dimension (FD) is a measure of how complicated vs. simple a self-similar multi-scale object is. Greater FD generally indicates increasing complex structure; smaller FD indicates decreased complexity (more 'simple' structure).

In time series analysis, FD can be used to quantify and monitor the irregularity or complexity of a waveform. In an embodiment, it is found (a) that various physiologic monitoring signals exhibit characteristic FD distributions during epochs when physiologic function of the patient is stable, even if abnormal; (b) that the location or dispersion of the FD distribution is altered at the time of, and often shortly before the onset of, changes in physiologic functioning that is abnormal or transiting into a regime that results in physiologic values that are out-of-range or transgress alarm thresholds; and (c) that the alteration of the location or dispersion of the FD distribution persists for a period of time after the onset of a condition meriting emission of a monitor alarm.

As such, abnormal FD values serve as an accurate criterion or filter for adjudicating the validity or attention-worthiness of threshold-transgression alarms prior to their being emitted.

Furthermore, "personalized" physiology of a subject is revealed in the particular FD distribution obtained from longitudinal time series in the monitored individual. For plethysmographic SpO2 measurements, some stable subjects (perioperative surgical patients) have median FD~1.8 while other patients (medical ICU patients with obstructive lung disease COPD) have median FD~1.5. Devolution toward unstable, true-alarm status may entail either simpler time series structure (e.g., slow trend downward in SpO2; diminishing FD) or more complex time series structure (e.g., episodic/paroxysmal/transient desaturations and subsequent tachypnea and recoveries of SpO2 to within the normal range; increasing FD).

Other efforts include outlier-detection and multi-rule and Shewhart-type statistical process control (SPC) techniques may not be sufficiently sensitive to detect changes in FD distribution quickly enough to be optimal for the purpose of alarm filtering or decision support. MOSUM, moving-estimates, CUSUM, and related 'empirical fluctuation process' analysis methods are likely to be sensitive to cumulative changes that persist within the window of time that is monitored and are thus able to accurately identify significant distribution changes in a manner that is more or less synchronous or contemporaneous with the raw physiological variable time series data stream.

In an embodiment one or more of mean removal, linear trend removal, and removal of auto-regressive (AR) signal content are used as a pre-processing step. An embodiment is able to remove the artifactual disturbance or biasing of the FD. Analysis performed on FD may be affected in result if these steps are omitted. An embodiment of detrending uses simple linear regression to calculate a least squares fit to any trend with respect to time in the record. A trend is subtracted from the record. An embodiment of pre-whitening employs a first-order difference filter (i.e., the value at t−1 is subtracted from the value at t) to remove any low-frequency information from the record.

Appropriate values for equal-sampling and "baseline" and "MOSUM" record-length considerations are advantageously set for each application. The monitored processes may be sampled at equal intervals for the resulting FD distributions to be easily statistically compared and correct inferences made with regard to the presence or absence of difference or change. Unfortunately, interpolation of the record can lead to the introduction of noise. Therefore, any imputation or interpolation to accommodate series that contain missing or erroneous values or disparate sampling rates may be performed with considerable care and detailed study to insure that time-scaling or imputation methods do not corrupt the interpretation of FD distributions. Finally, while the performance of these FD-based, empirical fluctuation process (EFP) based methods is greatly enhanced by longer record lengths (in terms of mean-square-error MSE for estimation of FD(t)), utilization of longer record lengths is at odds with the aim of achieving an output that is prompt and in near-real time synchrony with the monitored signal. Thus, a compromise between the maximum tolerable time delay for adjudication of a threshold transgression alarm and the minimum time duration to acquire a suitable length of baseline FD and FD-MOSUM data is necessary. Such compromise, in turn, depends on the sampling rate for acquisition of data. A monitoring device that generates new time series values at the rate of 1 per second will, naturally, accumulate a 300-sample time series in only 5 minutes, whereas a device that produces new time series values at the rate of 1 per 30 seconds will require 150 min to accumulate a 300-sample-long time series.

From data acquired from in-patient hospital subjects and stored in a data warehouse, baseline time series as short as 100 samples long were found effective in establishing a stable FD distribution, provided that the coefficient of variation present in the time series was at least 0.5% and provided further that the time series segment utilized for the calculation of each FD(t) time series value encompasses at least 10, but preferably 20 or more, or more preferably 50 or more data points.

$SpO_2$ time series that are precisely constant for the entirety of a "baseline" monitored interval may yield an FD equal to the theoretical value for a straight line (1.00); however, such FD determinations are inordinately sensitive to the presence of one or a few values that differ slightly from the predominant, constant value and, as such, are not reliable estimates of the true fractal dimension of the multiple, inter-related, cross-coupled physiologic processes underway. The same was found for heart rate, systolic blood pressure, mean arterial pressure, temperature, and other physiological variables that have been studied using embodiments of the invention. Using an embodiment, 72 hours of continuous $SpO_2$ monitoring, had only 3 false detections declared (False Positive rate=0.04 $hr^1$)

An embodiment consists of a device for assessing a patient, including subsystems comprising: a sensor for acquiring a physiological signal from a patient functionally coupled to a programmable element; wherein programmable elements: obtain a calibration coefficient; automatically adjust the acquisition circuitry; analyze the physiological signal to provide an assessment of at least one physiologic parameter of a patient; and quantitatively analyze and characterize the fractal dimension of a univariate time series signal that is the subject of alarm decision support and filtering.

An embodiment of a method for assessing a patient includes pre-processing that performs one or more of whitening, removing the mean, removing a trend and removing an autoregressive AR(N) component from a segment of the time series.

An embodiment performs a method of assessing a patient wherein the analysis of the fractal dimension time series includes calculation of structural change by means of MOSUM, moving-estimate, F-test, or other trend analysis breakpoint-detection statistics performed on an empirical fluctuation process constructed from the time series.

An embodiment performs a method of assessing a patient wherein the analysis of the spectra includes comparison of the breakpoint-detection results with an alarm status of the monitor that produced the raw signal.

An embodiment performs a method of assessing a patient wherein a time series is sampled longitudinally with a precision and dynamic range of at least 3 binary digits (bits; 12.5% resolution).

An embodiment performs a method of assessing a patient wherein a time series is sampled longitudinally with a precision and dynamic range of at least 12 bits (0.02% resolution) and exhibits a coefficient of variation (CV %) of at least 0.5%.

An embodiment performs a method of assessing a patient wherein a timeseries subset comprises longitudinal subsamples of length M representing time span sufficient to afford numerically stable estimates of FD. In an embodiment M is chosen such that $10<M<N1/2$.

An embodiment consists of a device for assessing a patient wherein the assessment determines an index of physiologic sufficiency which is used as a diagnostic or monitoring tool.

An embodiment consists of a device for assessing a patient wherein a programmable element, based on an assessed at least one hemodynamics parameter, at least one of determines the effect of one or more drugs or medical interventions on the patient, provides information supporting adjusting the patient's cardiovascular medications, suggests instituting or discontinuing mechanical circulatory assist in the patient, provides information supporting adjusting the patient's therapies or medications, suggests adjusting the patient's therapies or medications, provides information supporting adjusting mechanical circulatory assist settings, suggests adjusting mechanical circulatory assist settings, provides information supporting adjusting weaning the patient off a mechanical circulatory assist device, suggests weaning the patient off circulatory assist, provides information to assess a patient's status before, during, or after surgery or medical procedure, monitors for adverse hemodynamic conditions, monitors for inadequate perfusion, monitors exercise, and monitors disease or medical condition.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. Non-transitory Computer-readable media having computer-executable instructions embodied thereon that when executed, facilitate a method of clinical decision-making, the method comprising:
   monitoring input from at least one medical device, wherein the input comprises a set of physiological measurements of a patient;
   forming an estimate of a first variable, wherein the first variable is a dimension parameter over a first time interval based, at least in part, on a measure of roughness of a first plurality of the set of physiological measurements;
   providing a first decision statistic based on the estimate of the first variable;
   forming an estimate of a second variable, wherein the second variable is a second decision statistic over the first time interval based on the first plurality of the set of physiological measurements; and
   generating an audio or visual notification in response to the first decision statistic crossing a breakpoint threshold and the second decision statistic crossing a physiological threshold over the first time interval, wherein the physiological threshold is based at least partially on the first plurality of physiological measurements.

2. The non-transitory computer-readable media of claim 1, wherein providing said first decision statistic comprises calculating a trend statistic for a single physiological measurement over a moving window that comprises at least the first time interval and a second interval.

3. The non-transitory computer-readable media of claim 2, wherein said trend statistic is chosen from the set consisting of a moving sum, a moving estimate, an F-test and a cumulative sum.

4. The non-transitory computer-readable media of claim 1, wherein said dimension parameter is further based on a fractal dimension parameter.

5. The non-transitory computer-readable media of claim 4, wherein said forming the estimate comprises using an operation chosen from the set consisting of wavelet transformation, Higuchi, Katz, K-Nearest Neighbor, rescaled-range (R/S), autocovariance function (ACVF), Whittle, Hall-Wood, box-count, Discrete Cosine Transform, Variogram, and Cevcik methods.

6. The non-transitory computer-readable media of claim 1, further comprising generating a maintenance indication responsive to determining that said second decision statistic has crossed physiological threshold level and that said first decision statistic has not crossed said breakpoint threshold.

7. The non-transitory computer-readable media of claim 1, further comprising providing information related to the decision statistics for presentation to a clinician on a computer output device.

8. A non-transitory computer-implemented method to evaluate an alarm condition for a monitored patient within a population of one or more patients, the method comprising:
   accessing a set of physiological measurements of a patient in the population, the set of physiological measurements collected as data from at least one medical device associated with the patient;
   generating a first decision statistic by forming an estimated first variable using a measure of roughness of a first plurality of the set of physiological measurements over a first time interval based;

generating a second decision statistic by forming an estimated second variable using the first plurality of the set of physiological measurements over a first time interval based; and generating an audio or visual notification in response to the first decision statistic crossing a breakpoint threshold and the second decision statistic crossing a physiological threshold over the first time interval.

9. The non-transitory computer-implemented method according to claim 8, further comprising presenting the notification to a human decision-maker via an electronic medical record software system or device.

10. The non-transitory computer-implemented method according to claim 8, further comprising calculating the second decision statistic and the value of the physiological measurements in one or more of a monitor device, a server, a distributed agent system, and a stream processor.

11. The non-transitory computer-implemented method according to claim 8, wherein the physiological input is chosen from the set consisting of a respiratory parameter, a hemodynamics parameter, heart rate, a blood pressure parameter, systolic blood pressure, diastolic blood pressure, respiratory rate, temperature, Sp02, Scv02, S02, pulmonary Capillary Web Pressure (PCWP), Left Atrium Pressure (AP), Central Venous Pressure (CVP), Intra-Cranial Pressure (ICP), and Mean Arterial Pressure (MAP).

12. The non-transitory computer-implemented method according to claim 11, further comprising providing information related to at least one of determining an effect of one or more drugs, determining an effect of one or more medical interventions, supporting extubating the patient, suggesting extubating the patient, supporting adjustment of patient therapy, supporting an adjustment to medication, suggesting an adjustment to patient therapy, supporting ventilator settings, suggesting adjusting ventilator settings, weaning the patient off ventilation, suggesting weaning the patient off ventilation, assessing patient status before surgery, assessing patient status during surgery, assessing patient status after surgery, assessing patient status before a medical procedure, assessing patient status during a medical procedure, assessing patient status after a medical procedure, monitoring for air leaks, monitoring for improper ventilation, monitoring exercise, monitoring stress levels, monitoring a medical condition and monitoring disease.

13. Non-transitory computer-readable media having computer-executable instructions embodied thereon that when executed, facilitate a method of clinical decision-making, the method comprising:

monitoring one or more physiological measurement inputs of a patient;

forming a first variable, wherein the first variable is an estimate of a dimension parameter over a first time interval based, at least in part, on a measure of roughness of a first set of the one or more physiological measurement inputs;

providing a decision statistic based on said first variable;

forming a second variable, wherein the second variable is an estimate of a physiological decision statistic over the first time interval based on the first set of the one or more physiological measurement inputs;

determining whether said decision statistic has crossed a breakpoint threshold;

determining whether said physiological decision statistic has crossed a physiological measurement threshold, wherein the notification threshold level is based at least partially on the one or more physiological measurement inputs; and in response to determining that the physiological measurement threshold has been crossed and the breakpoint threshold has not been crossed, generating an audio or visual equipment notification corresponding to a failure of equipment associated with the one or more physiological measurement inputs.

14. The non-transitory computer-readable media according to claim 13, wherein the or ore more physiological measurement inputs is chosen from the set consisting of a respiratory parameter, a hemodynamics parameter, heart rate, a blood pressure parameter, systolic blood pressure, diastolic blood pressure, respiratory rate, temperature, Sp02, Scv02, S02, pulmonary Capillary Web Pressure (PCWP), Left Atrium Pressure (AP), Central Venous Pressure (CVP), Intra-Cranial Pressure (ICP), and Mean Arterial Pressure (MAP).

15. The non-transitory computer-readable media according to claim 13, wherein said dimension parameter is further based on a fractal dimension parameter.

16. The non-transitory computer-readable media according to claim 13, wherein providing said decision statistic comprises calculating a trend statistic for a single physiological measurement over a moving window that comprises at least said first time interval and a second time interval.

17. The non-transitory computer-readable media according to claim 16, wherein said trend statistic is chosen from the set consisting of a moving sum, a moving estimate, an F-test and a cumulative sum.

18. The non-transitory computer-readable media according to claim 13, further comprising:

generating another audio or visual notification in response to determining that the physiological measurement threshold while the breakpoint threshold is crossed over the first time interval.

19. The non-transitory computer-readable media according to claim 18, further comprising presenting the notification to a human decision-maker via an electronic medical record software system or device.

20. The non-transitory computer-readable media according to claim 13, further comprising presenting the notification to a human decision-maker via an electronic medical record software system or device.

* * * * *

UNITED STATES PATENT AND TRADEMARK OFFICE
CERTIFICATE OF CORRECTION

PATENT NO. : 10,653,368 B1
APPLICATION NO. : 14/481436
DATED : May 19, 2020
INVENTOR(S) : Douglas S. McNair It is certified that error appears in the above-identified patent and that said Letters Patent is hereby corrected as shown below:

In the Specification
Column 03, Line 10: Please remove "patient;" and replace with --patient.--.
Column 08, Line 06: Please remove "SHRs" and replace with --EHRs--.
Column 08, Line 08: Please remove "SHRs" and replace with --EHRs--.
Column 08, Line 10: Please remove "SHRs" and replace with --EHRs--.
Column 09, Line 41: Please remove "hypotaxia/desaturation." and replace with --hypoxia/desaturation.--.
Column 09, Line 60: Please remove "Capilary" and replace with --Capillary--.
Column 13, Line 66: Please remove "maintentance" and replace with --maintenance--.
Column 15, Line 41: Please remove "Cevcik" and replace with --Sevcik--.
Column 21, Line 33: Please remove "N1>100; 10<M<N1/2; 10<N2<M." and replace with --N1$\geq$100; 10$\leq$M<N1/2; 10$\leq$N2$\leq$M.--.
Column 22, Line 05: Please remove "autogregressive" and replace with --autoregressive--.
Column 24, Line 47: Please remove "hr$^1$" and replace with --hr$^{-1}$--.

In the Claims
Column 26, Line 02: Please remove "Computer-readable" and replace with --computer-readable--.
Column 26, Line 32: After "second" please insert --time--.
Column 26, Line 46: Please remove "Cevcik" and replace with --Sevcik--.
Column 27, Line 23: Please remove "Sp02, Scv02, S02," and replace with --SpO2, ScvO2, SO2,--.
Column 28, Line 20: Please remove "or one" and replace with --one or--.
Column 28, Lines 24-25: Please remove "Sp02, Scv02, S02," and replace with --SpO2, ScvO2, SO2,--.

Signed and Sealed this
Seventh Day of July, 2020

Andrei Iancu
*Director of the United States Patent and Trademark Office*